United States Patent [19]

Walden

[11] 4,108,176

[45] Aug. 22, 1978

[54] AUTOMATIC INJECTING APPARATUS

[75] Inventor: Carl W. Walden, Ulysses, N.Y.

[73] Assignee: Agri-Bio Corporation, Jacksonville, N.Y.

[21] Appl. No.: 772,364

[22] Filed: Feb. 25, 1977

[51] Int. Cl.² .............................................. A61M 5/00

[52] U.S. Cl. .......................... 128/218 A; 128/DIG. 1

[58] Field of Search ........... 128/218 A, 218 F, 218 P, 128/218 R, 215, 213, 253, 234, DIG. 1

[56] References Cited

U.S. PATENT DOCUMENTS

| | | | |
|---|---|---|---|
| 3,051,173 | 8/1962 | Johnson et al. | 128/218 F |
| 3,641,998 | 2/1972 | Lyon et al. | 128/218 A |
| 3,964,481 | 6/1976 | Gourlandt et al. | 128/218A |

FOREIGN PATENT DOCUMENTS

| | | | |
|---|---|---|---|
| 1,242,060 | 8/1971 | United Kingdom | 128/218 A |

*Primary Examiner*—John D. Yasko
*Attorney, Agent, or Firm*—John J. Byrne

[57] ABSTRACT

An automatic injection device for small animals. The device comprises a work plate on which an animal to be injected can be positioned, a syringe mounted on the opposite side of the work plate from the side on which the animal to be injected is positioned during use of the device, first means for moving the syringe back and forth between a first position in which the syringe needle is entirely withdrawn on said opposite side of the work plate and a second position in which the syringe needle protrudes through an aperture in the work plate, and second means for detecting the presence of an animal to be injected in position on the work plate and for activating the first means. The first means comprises a single-action pneumatic motor and means for retaining the syringe in its second position while the mounting of the syringe is adjusted. Means for venting an accidental increase in pressure in the pneumatic supply, means for indicating the completion of a preset number of injections, means permitting the quick replacement of the syringe, and a transparent valve plate permitting the user to view at least a portion of the second means are provided.

39 Claims, 8 Drawing Figures

FIG. 8
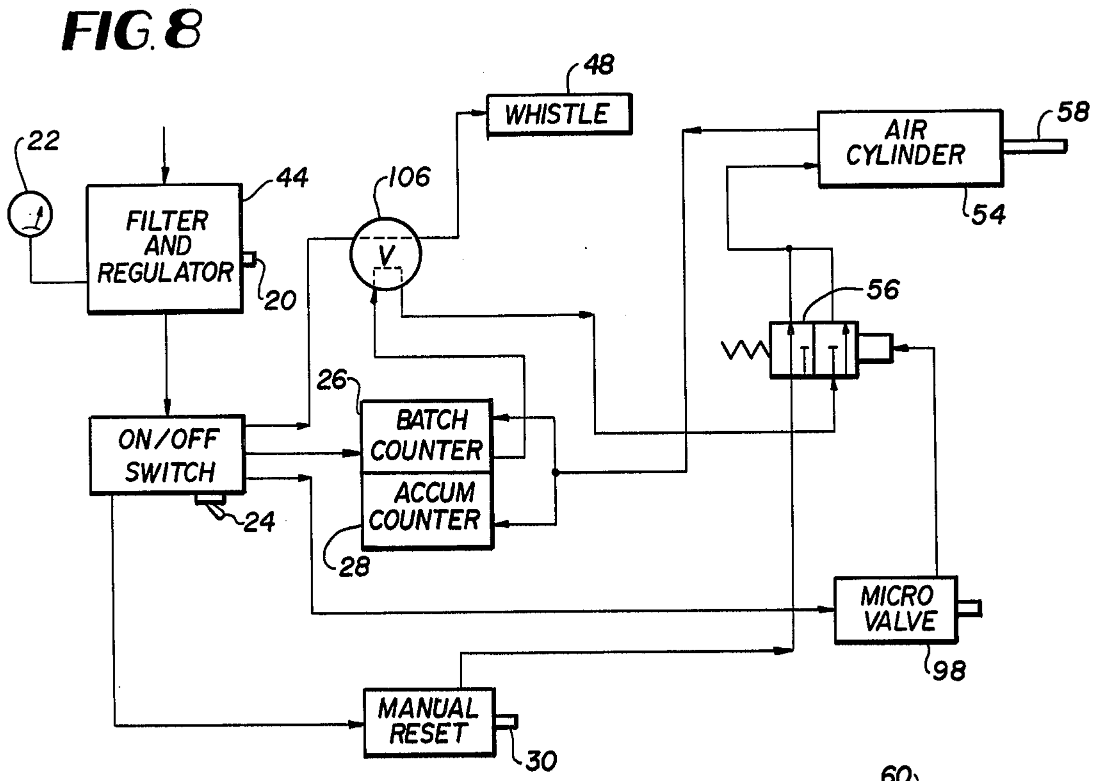
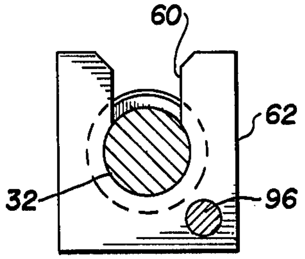
FIG. 5
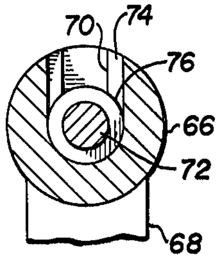
FIG. 6
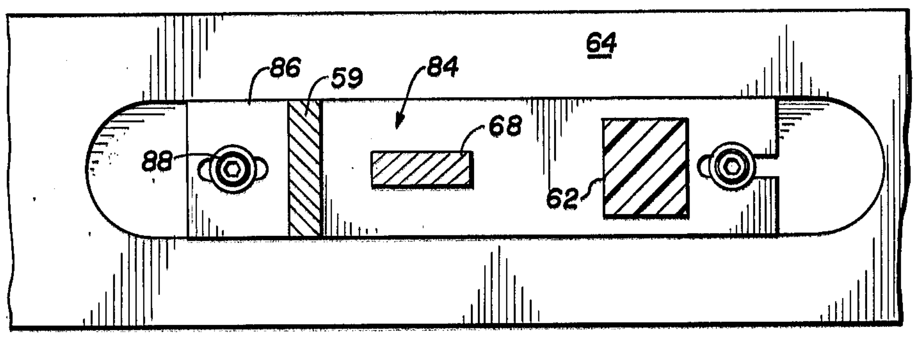
FIG. 7

AUTOMATIC INJECTING APPARATUS

BACKGROUND OF THE INVENTION

This invention relates to a device for sequentially injecting a large number of small animals, such as chicks, ducklings, young turkeys, and guinea fowl with a desired substance. Such devices are in common use, particularly in the hatchery industry, and representative examples of such devices are disclosed, for instance, in U.S. Pat. Nos. 3,641,998 to Lyon et al. and 3,964,481 to Gourlandt et al.

Devices of this general type typically comprise a work plate on which an animal to be injected can be position, a needle-type syringe (spray-type syringes may also be used in functionally similar devices) mounted on the opposite side of the work plate from the side on which the animal to be injected is positioned during use of the device, first means for moving the syringe back and forth between a first position in which the syringe needle is entirely withdrawn on the opposite side of the work plate and a second position in which the syringe needle protrudes through an aperture in the work plate, and second means for detecting the presence of an animal to be injected in position on the work plate and for activating the first means. In the past, the first means has been an electric motor, but such motors have proved to be not entirely satisfactory for several reasons. In the first place, such motors have caused some safety problems, particularly in the wet environment of hatcheries. In the second place, while such machines may be portable, they can be used only in the vicinity of a source of wall current. And, in the third place, such motors have imposed a limitation on the number of animals which can be injected per unit of time which is less than the rate which a skilled operator is capable of achieving. Accordingly, it has long been known that it would be desirable to find an alternate syringe actuator not suffering from these drawbacks.

It is known in the art that sometimes variations of penetration and/or dosage is required, as in successive treatments or for different sizes and ages of the animals being injected, and various means are employed to permit such variations. However, the means now in use have been found to be unduly complex, not completely accurate, and to be somewhat lacking in reliability, particularly with respect to variations in the extent of penetration.

Despite the best efforts of the user of such devices, the environment in which they are used is typically far from clean, and the devices are often subject to rough usage. Accordingly, it has often been necessary to open up the device to inspect and, if necessary, clear or repair operative components. This operation, of course, takes time and is particularly irritating when, after opening up the machine, it is found that no cleaning or repairing is necessary.

The syringe has to be taken out, cleaned, sterilized, and replaced one or two times daily. Accordingly, it is imperative that the syringe be easily and quickly removed and replaced, and various "quick connect" devices for attaching the syringe to the activating apparatus have been proposed. All, however, have been more or less unsatisfactory due to excessively complicated parts, excessive operation time, and/or a tendency to cause bending of the syringe shafts during use.

The problems suggested in the preceding are not intended to be exhaustive, but rather are among many which tend to reduce the effectiveness of prior injection devices. Other noteworthy problems may also exist; however, those presented above should be sufficient to demonstrate that injection devices appearing in the prior-art have not been altogether satisfactory.

OBJECTS OF THE INVENTION

It is, therefore, a general object of the invention to provide an automatic device for sequentially injecting a large number of small animals with a desired substance which will obviate or minimize problems of the type previously described.

It is a particular object of the invention to provide such a device which will operate safely and reliably in the wet environment of hatcheries.

It is a further object of the invention to provide such a device which is both portable and capable of operation wherever the user desires to use it.

It is yet a further object of the invention to provide such a device which is capable of being operated at a faster rate than the prior-art, electrically powered devices.

It is still a further object of the invention to provide such a device in which the extent of penetration can be easily, accurately, and reliably varied.

It is another object of the invention to provide such a device in which the need for opening up the device to inspect the operative components for dirt, wear, and damage due to other causes is lessened.

It is still another object of the invention to provide such a device in which the syringe can be removed and replaced with extreme rapidity and in which the parts providing this facility are extremely simple to manufacture, sturdy in use, and extremely unlikely to cause damage to the syringe.

It is still a further object of the invention to provide such a device in which the necessary adjustments of relative parts positions are few in number and easy to make.

Other objects and advantages of the present invention will become apparent from the following detailed description of a preferred embodiment taken in conjunction with the accompanying drawings.

THE DRAWINGS

FIG. 5 is a sectional view taken generally along the line 5—5 in FIG. 2.

FIG. 6 is a sectional view taken generally along the line 6—6 in FIG. 2.

FIG. 7 is a sectional view taken generally along the line 7—7 in FIG. 2.

FIG. 8 is a schematic drawing of the air logic of the embodiment shown in FIGS. 1-7.

DETAILED DESCRIPTION

Figure 1:
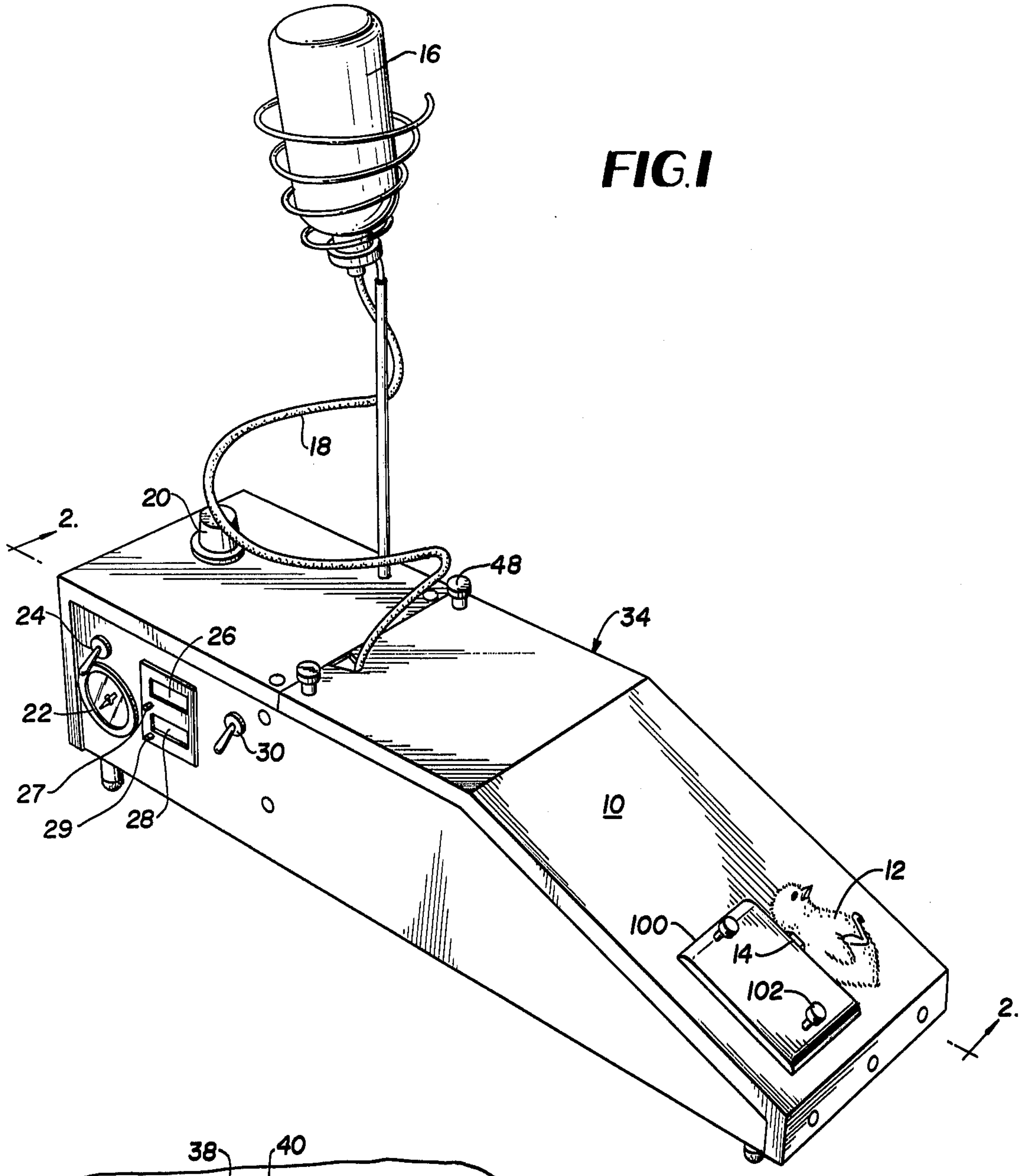
FIG. 1 is a perspective view of the presently preferred embodiment of the invention, showing a chick in position for an injection.

Referring now particularly to FIG. 1, there will be seen an automatic injection device comprising a work plate 10 on which a chick 12 is shown positioned ready for an injection, means 14 for detecting the presence of the animal to be injected in position on the work plate 10 and for actuating means (not visible in FIG. 1) for injecting the animal, a container 16 for a liquid, such as a vaccine, to be injected into the animal, a tube 18 for conducting the liquid from the container 16 to a syringe (not visible in FIG. 1), a pressure regulator control 20, a pressure gauge 22, an on-off switch 24, a batch counter 26, a batch reset button 27, an accumulative counter 28, an accumulator reset button 29, and a test switch 30 the purpose of which will be described hereinafter.

Figure 2:
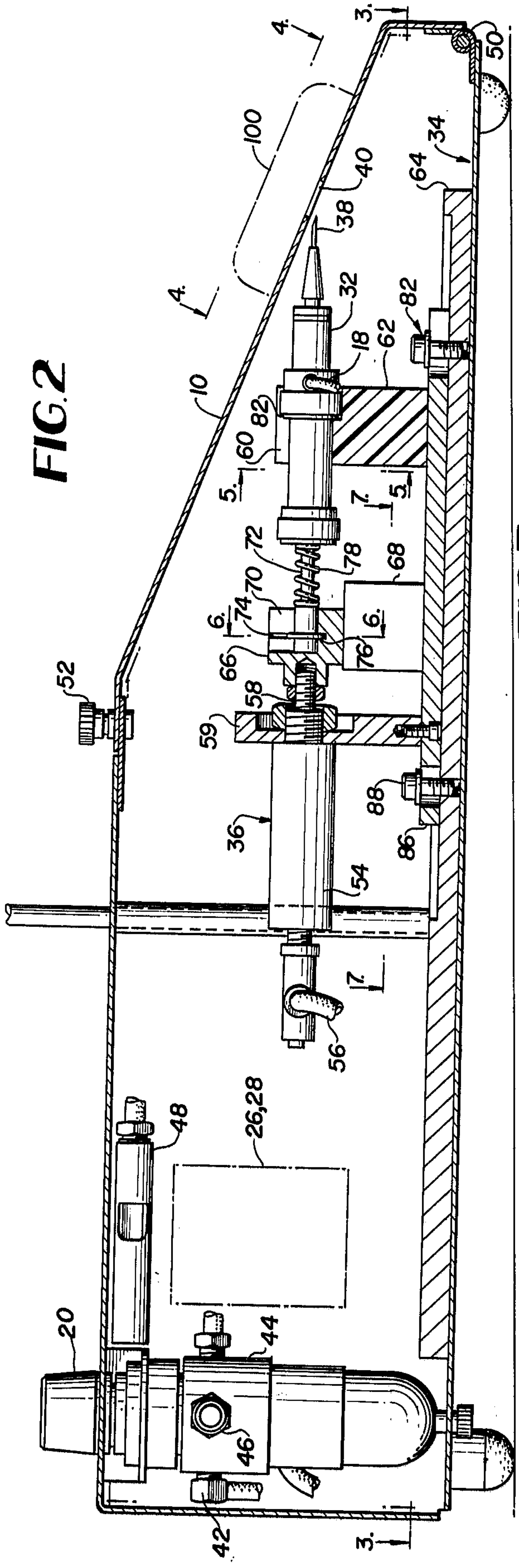
FIG. 2 is a side cross-sectional view taken generally along the lines 2—2 of FIG. 1.

Turning next to FIG. 2, there will be seen a syringe 32 of the needle-variety mounted on the opposite side of the work plate 10 from the side on which the animal to be injected is positioned during use of the device and within a stainless steel cabinet 34, motor means 36 for moving the syringe 32 back and forth between a first position in which the syringe needle 38 is entirely withdrawn within the cabinet 34 and a second position in which the syringe needle 38 protrudes through an aperture 40 in the work plate 10, a high-pressure connector 42 (which may be connected to any convenient external source of high-pressure air, including a portable tank of high-pressure air), an air filter and pressure control mechanism 44 with a safety valve 46 which vents accidental increases in pressure in the high-pressure air, and an indicator whistle 48 the purpose of which will be explained hereinafter. It will also be seen that the work plate 10 is mounted on the cabinet 34 by means of hinges 50 and held in place during use of the device by a conventional latch mechanism 52. The motor means 36 comprises a pneumatic motor which, in the preferred embodiment, is an air cylinder 54 connected to the air filter and pressure control mechanism 44 pneumatic circuitry described hereinafter, and an actuator 56 (shown only in FIG. 8) which produces a short, phased motion of the cylinder rod 58 regardless of how long the means 14 is actuated. Such actuators are conventional elements in pneumatic circuitry, and accordingly it is not believed necessary to describe them in further detail. The air cylinder 54 is mounted in a motor support 59 which in turn is mounted on a slotted block 86 the purpose of which will be described hereinafter.

The purpose of the air control and filter mechanism 44 is to make sure that the air entering the pneumatic circuitry is clean and at the desired operating pressure regardless of the condition of the air entering the machine. Its filter section has a mesh, the gauge of which is 40 microns in the presently preferred embodiment, to exclude dirt, dust, and oil from the system, and its regulator section can be used to adjust incoming pressure to the desired level, which is 30 to 60 psi in the presently preferred embodiment.

As best seen in FIG. 5, the syringe 32 is journaled for rapid translational movement in an open-topped slot 60 in an upwardly extending block 62 mounted on the slotted block 86. The block 62 is made of a resilient material such as a resilient plastic, so that the syringe 32 is snapped into place in the block 62 and held in place by the resiliency of the block. The rod 58 of the air cylinder 54 is threaded into a syringe coupling attachment 66 which is slidingly supported on a block 68 mounted on the slotted block 86 as best seen in FIGS. 2 and 6. The syringe coupling attachment 66 has a longitudinal open-topped slot 70 to receive one end of a shaft 72 and a transverse open-topped slot 74 to receive a collar 76 carried by the shaft 72. The open-topped slots 60 and 70 together permit the syringe 32 and the shaft 72 to be simply lifted in and out of place in the block 62 and the syringe coupling attachment 66, respectively, and the cooperation of the collar 76 and the transverse slot 74 fix the longitudinal position of the shaft 72 and the syringe 32 relative to the air cylinder 54. The shaft 72, which is part of the syringe plunger, is telescopically received within the syringe 32, and a compression spring 78 is carried by the shaft 72 and confined between the forward face of the syringe coupling attachment 66 and the rear face of the syringe 32.

Figure 3:
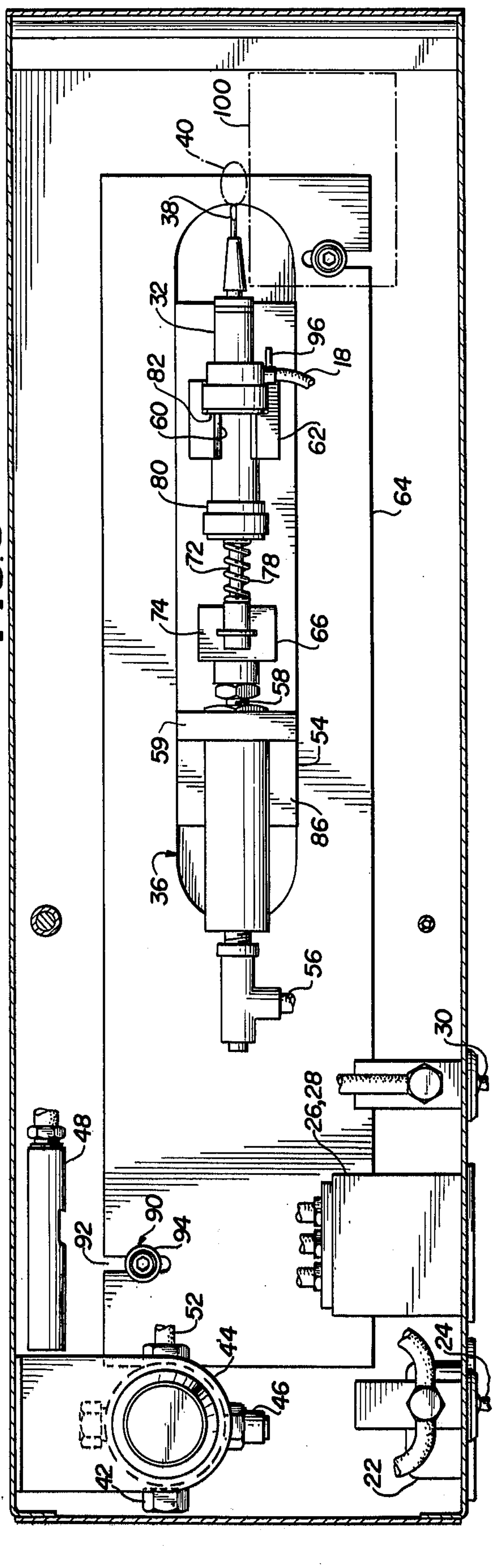
FIG. 3 is a top elevational view with the cover broken away to expose the interior of the device.

In use, actuation of the means 14 triggers actuation of the air cylinder 54, which initially causes the rod 58, the syringe coupling attachment 66, the shaft 72, and the syringe 32 to move forward as a unit until the needle of the syringe 32 protrudes through the aperture 40 and into the animal by the desired amount. At that point, a collar 80 at the base of the syringe 32 comes into abutment with the rear face of the block 62, and forward movement of the syringe 32 is halted. However, the rod 58, the syringe coupling attachment 66, and the shaft 72 continue to move forward, and the shaft 72 travels telescopically into the butt of the syringe 32 against the force of the compression spring 78. Within the syringe 32, the shaft 72 actuates a syringe piston to expel a metered amount of liquid through the syringe needle in a manner known per se. The air cylinder then returns to its rest position under the influence of an internal spring (not shown), allowing the spring 78 to separate the syringe coupling attachment 66 and the collar 80 of the syringe 32 and drawing the syringe 32 back to its rest position. As best seen in FIG. 3, the rest position of the syringe 32 is determined by the abutment of the forward face of a recess in the block 62 and the rearward face of a collar 82 on the syringe 32.

The longitudinal position of the air cylinder 54 and the rest position of the syringe 32 are advantageously adjustable via the mechanism 84, best seen in FIGS. 2 and 7. As shown therein, the mechanism 84 comprises the slotted block 86 to which the motor support 59, the block 68, and the block 62 are fixedly mounted and a plurality of bolts 88 which pass through the block 86 and are received in a support block 64. The slots in the block 86 are parallel to the direction of motion of the syringe 32, and by loosening the bolts 88, sliding the subcombination comprising the block 86, the air cylinder 54, and the syringe 32 along the surface of the support block 64, and then retightening the bolts 88, the extent to which the needle of the syringe 32 protrudes through the aperture 40 during use of the device can be adjusted.

The transverse position of the air cylinder 54 and the syringe 32 are advantageously adjustable via a similar slot-and-bolt mechanism 90 best seen in FIG. 3. As shown therein, the mechanism 90 comprises slots 92 in the support block 64 and a plurality of bolts 94 which pass through the slots 92 and are received in the base of the cabinet 34. The slots 92 are perpendicular to the direction of motion of the syringe 32, and the mechanism 90 work in the same manner as the mechanism 84. However, it has been found in practice that, once the mechanism 90 has been set in the factory, it is seldom necessary to adjust it again unless the device is subjected to severe abuse.

To prevent rotation of the syringe 32 in the syringe coupling attachment 66, a projection 96 is provided on the block 62. In practice it has been found that the syringe 32 tends to rotate by a few degrees in the same direction each time the air cylinder 54 is activated, and the tube 18 quickly comes into contact with the projection 96, preventing further rotation of the syringe 32.

To aid the user of the device in varying the penetration of the needle 32 into the animals being injected, the previously mentioned test switch 30 is provided. Actuation of the test switch 30 causes air to be continuously fed into the air cylinder 54. Accordingly, the air cylinder 54 extends, but it does not return to its normal position until the test switch 30 is deactivated. With the air cylinder 54 extended, the syringe 32 is also extended, and the user can visually determine whether or not its needle 38 extends through the aperture 40 by the desired amount and, if it does not, the amount by which it must be adjusted in either direction.

Figure 4:
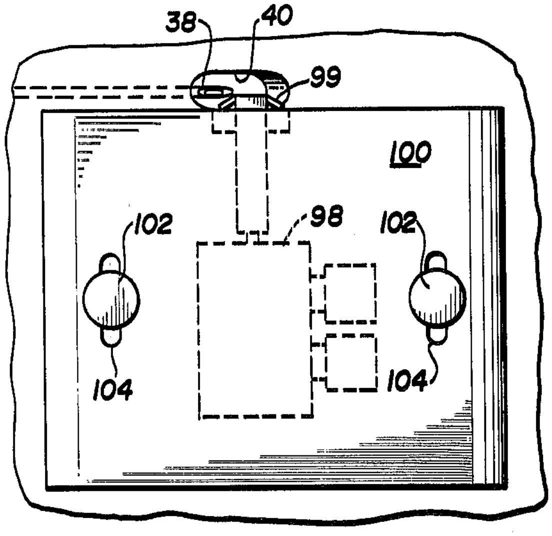
FIG. 4 is a top elevational view of the "CLEAN-VUE"™ valve plate taken generally along the line 4—4 of FIG. 2.

The means 14 for detecting the presence of the animal to be injected in position on the work plate 10 and for actuating the air cylinder 54 is best seen in FIG. 4. In the subject invention, this means comprises a microvalve 98 the actuator 99 of which is depressed by the body of the animal to be injected when it is correctly positioned against the edge of the valve plate 100. The microvalve 98 is operatively coupled to the air cylinder 54 via the actuator 56, the batch counter 26, and the accumulative counter 28 by appropriate pneumatic circuitry which causes the air cylinder to actuate and the counters to count one upon the depression of the microvalve. The valve plate 100 is transversely adjustable via thumb screws 102 which pass through slots 104 in the valve plate 100 and are received in the work plate 10. The valve plate 100 is at least partially transparent, allowing the user of the device to view the microvalve 98, which is mounted on the outside of the work plate 10, and to visually determine whether or not it needs cleaning without removing the thumb screws 102.

As previously mentioned, both a batch counter 26 and an accumulative counter 28 are provided on the device. The batch counter 26 may be manually set at any desired number, as for instance the number of chicks to be placed in each box after having been injected, and it counts down from that number to zero. The batch counter 26 is operatively connected to the whistle 48 to provide an audible indication of when the batch count is reached. As explained hereinafter in connection with the air logic, when the whistle sounds, the machine automatically shuts off to prevent extra units (chicks) from entering the batch, and the machine will operate again only when the batch reset button 27 has been pushed. The accumulative counter 28 is designed to count up to measure the number of injections in any desired period, as for instance a day, and it may be reset at zero by means of the accumulator reset button 29.

The air logic of the foregoing device is shown in FIG. 8. As will be seen therein, the compressed air supply is connected to the air control and filter mechanism 44, and the internal pressure of the device may be adjusted by the pressure regulator control 20. The air leaves the air control and filter mechanism 44 and goes to the on-off switch 24. From there, the air branches into four separate paths. One path goes to the test switch 30, through a normally open path in the actuator 56, and from there to the air cylinder 54. Thus, when the on-off switch 24 is turned to on and the test switch 30 is actuated, pressurized air flows directly and continuously to the air cylinder 54. The second path goes to the microvalve 98 and from there to the actuator 56, where it causes a normally closed gate in the actuator 56 to open for a predetermined interval. The third path goes to a pilot valve 106 which has two inputs and two outputs. One output goes through the normally closed gate in the actuator 56 and from there to the air cylinder 54. The air cylinder 54 is also connected to the batch counter 26 and the accumulative counter 28, and actuation of the air cylinder causes the batch counter to count down one and the accumulative counter to count up one. The fourth path from the on-off switch 24 goes to the batch counter 26, and when the batch counter 26 has counted down to zero, air is passed through the pilot valve 106 to the whistle 48, audibly signaling the end of the count, shutting down the machine until it is manually re-activated by the batch reset button 27.

From the foregoing description of an automatic injection device for small animals in accordance with a preferred embodiment of the invention, those skilled in the art will recognize several advantages which singularly distinguish the subject invention from previously known devices. Some of those advantages are set forth below. However, while the following list of advantages is believed to be both accurate and representative, it does not purport to be exhaustive.

A particular advantage resides in the ability of the device to operate safely and reliably in the wet environment of hatcheries.

A further advantage of the device resides in its portability and its capability of operating wherever the user desires to use it — i.e., its independence from a fixed energy source.

A further advantage of the device is the fact that it is capable of being operated at a faster rate than the prior art, electrically powered devices.

Yet a further advantage of the device is the fact that the extent of syringe needle penetration can be easily, accurately, and reliably varied.

Another advantage of the device is that the need for opening it up to inspect the operative component for dirt, wear, and damage due to other causes is lessened.

Still another advantage of the device is that the syringe can be removed and replaced with extreme rapidity and that the syringe mounting mechanism is extremely simple to manufacture, sturdy in use, and unlikely to damage the syringe.

Yet another significant aspect of the invention is that pneumatic actuation of the syringe produces an audible signal which enables an operator to facilely discern when an injection is made.

Another advantage of the device is that the necessary adjustments of relative parts positions are few in number and easy to make.

Still another advantage of the device is that it insures accuracy of batch counts by automatically shutting down at the end of each batch until the device is reactivated.

Finally, it should be noted that, while the present invention has been illustrated by a detailed description of a preferred embodiment thereof, it will be obvious to those skilled in the art that various changes in form and detail can be made therein without departing from the true scope of the invention. For that reason, the invention must be measured by the claims appended hereto and not by the foregoing preferred embodiment.

What is claimed is:

1. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein said first means comprises:

(e) a fluid motor;

(f) third means for filtering the fluid input to said fluid motor;

(g) fourth means for controlling the pressure of the fluid input to said fluid motor; and (h) fifth means for venting an accidental increase in the pressure of the fluid input to said fourth means.

2. In a device as recited in claim 1, the further improvement wherein:

said first means comprises means for retaining said syringe in its second position.

3. In a device as recited in claim 2, the further improvement comprising:

sixth means for adjusting the amount by which the needle of said syringe protrudes through the aperture in said work plate when said syringe is in its second position.

4. A device as recited in claim 3, wherein said sixth means comprises:

a first slotted block on which said first means is carried and a plurality of bolts which pass through the slots in said first slotted block.

5. In a device as recited in claim 1, the further improvement comprising:

sixth means for adjusting the amount by which the needle of said syringe protrudes through the aperture in said work plate when said syringe is in its second position.

6. A device as recited in claim 5, wherein said sixth means comprises:

a first slotted block on which said first means is carried and a plurality of bolts which pass through the slots in said first slotted block.

7. In a device as recited in claim 5, the further improvement comprising:

seventh means for adjusting the position of said syringe in the horizontal plane and in the direction perpendicular to its direction of motion.

8. A device as recited in claim 7, wherein said seventh means comprises:

a second slotted block on which said first means is carried and a plurality of bolts which pass through the slots in said second slotted block.

9. In a device as recited in claim 1, the further improvement comprising:

sixth means for adjusting the position of said syringe in the horizontal plane and in the direction perpendicular to its direction of action.

10. A device as recited in claim 9, wherein said sixth means comprises:

a first slotted block on which said first means is carried and a plurality of bolts which pass through the slots in said first slotted block.

11. In a device as recited in claim 1, the further improvement wherein:

said second means comprise a microvalve carried on said work plate on the same side as the animal to be injected is positioned during use of the device and a housing carried by said work plate and containing said microvalve, at least a portion of said housing being transparent, whereby the user of the device can view said microvalve through said housing.

12. In a device as recited in claim 11, the further improvement wherein:

(e) said syringe is journaled for rapid translational movement in an open-topped slot in a block mounted on said opposite side of said work plate and (f) said syringe is connected to said first means by means comprising:

(i) a syringe coupling attachment which has a longitudinal open-topped slot and a transverse open-topped slot intersecting the longitudinal open-topped slot, said syringe coupling attachment being carried by said first means, and (ii) a shaft carried by said syringe and having a collar, said shaft being sized and positioned to fit into the longitudinal open-topped slot in said syringe coupling attachment and said collar being sized and positioned to fit into the transverse open-topped slot in said syringe coupling attachment, whereby said syringe and said shaft may be simply lifted in and out of place in said block and said syringe coupling attachment, respectively.

13. In a device as recited in claim 12, the further improvement wherein:

said block is made out of a resilient material and the width of the open-topped slot therein is less than the width of said syringe, whereby said syringe is held against vertical motion by the resiliency of said block.

14. In a device as recited in claim 12, the further improvement wherein:

said first means comprises means for retaining said syringe in its second position.

15. In a device as recited in claim 1, the further improvement wherein:

(e) said syringe is journaled for rapid translational movement in an open-topped slot in a block mounted on said opposite side of said work plate and (f) said syringe is connected to said first means by means comprising:

(i) a syringe coupling attachment which has a longitudinal open-topped slot and a transverse open-topped slot intersecting the longitudinal open-topped slot, said syringe coupling attachment being carried by said first means, and (ii) a shaft carried by said syringe and having a collar, said shaft being sized and positioned to fit into the longitudinal open-topped slot in said syringe coupling attachment and said collar being sized and positioned to fit into the transverse open-topped slot in said syringe coupling attachment, whereby said syringe and said shaft may be simply lifted in and out of place in said block and said syringe coupling attachment, respectively.

16. In a device as recited in claim 15, the further improvement wherein:

said block is made out of a resilient material and the width of the open-topped slot therein is less than the width of said syringe, whereby said syringe is held against vertical motion by the resiliency of said block.

17. In a device as recited in claim 1, the further improvement comprising:

sixth means for counting the number of times said first means has been actuated.

18. A device as recited in claim 17, wherein said sixth means comprising:

seventh means for counting down from a preset number to zero.

19. A device as recited in claim 18, and further comprising:

means for providing an audible signal when said seventh means has reached zero.

20. In a device as recited in claim 18, the further improvement comprising:

means for shutting off the device when said seventh means has reached zero.

21. A device as recited in claim 18, wherein:

said sixth means comprises eighth means for counting up from zero.

22. A device as recited in claim 17, wherein said sixth means comprises:

seventh means for counting up from zero.

23. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein: said second means comprise a microvalve carried on said work plate on the same side as the animal to be injected is positioned during use of the device and a housing carried by said work plate and containing said microvalve, at least a portion of said housing being transparent, whereby the user of the device can view said microvalve through said housing.

24. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein:

(e) said syringe is journaled for rapid translational movement in an open-topped slot in a block mounted on said opposite side of said work plate and (f) said syringe is connected to said first means by means comprising:

(i) a syringe coupling attachment which has a longitudinal open-topped slot and a transverse open-topped slot intersecting the longitudinal open-topped slot, said syringe coupling attachment being carried by said first means, and (ii) a shaft carried by said syringe and having a collar, said shaft being sized and positioned to fit into the longitudinal open-topped slot in said syringe coupling attachment and said collar being sized and positioned to fit into the transverse open-topped slot in said syringe coupling attachment, whereby said syringe and said shaft may be simply lifted in and out of place in said block and said syringe coupling attachment, respectively.

25. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein said first means comprise:

(e) third means for producing a short, phased motion of said syringe regardless of how long said second means detects the presence of an animal to be injected in position on said work plate; and (f) fourth means for retaining said syringe in its second position.

26. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein said first means comprises:

(e) a fluid motor;

(f) third means for filtering the fluid input to said fluid motor; and (g) fourth means for controlling the pressure of the fluid input to said fluid motor.

27. In an automatic injection device comprising:

(a) a work plate on which an animal to be injected can be positioned, said work plate having an aperture therein;

(b) a syringe mounted on the opposite side of said work plate from the side on which the animal to be injected is positioned during used of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein:

(e) said syringe is journaled for rapid translational movement in a slot on a block mounted on said opposite side of said work plate; and (f) said syringe is connected to said first means by means comprising:

(i) a syringe coupling attachment which has an open recess therein, said syringe coupling attachment being carried by said first means, and (ii) a shaft carried by said syringe and having an enlargement thereon, said enlargement being sized and positioned to fit into the recess in said syringe coupling attachment, whereby said syringe and said shaft may be simply moved in and out of place in said block and said syringe coupling attachment, respectively.

28. In a device as recited in claim 27, the further improvement wherein:

said block is made out of a resilient material and the width of the slot therein is less than the width of said syringe, whereby said syringe is held by the resiliency of said block.

29. In a device as recited in claim 27, the further improvement wherein:

(a) the slot in said block is open-topped, and (b) the recess in said syringe coupling attachment is upwardly open, whereby said syringe and said shaft may be simply lifted in and out of place in said block and said syringe coupling attachment, respectively.

30. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein:

(e) said syringe is journaled for rapid tranlational movement in a slot in a block mounted on said opposite side of said work plate; and (f) said syringe is connected to said first means by means comprising:

(i) a coupling attachment carried by one of said syringe and said first means, said coupling attachment having an open recess therein; and (ii) a shaft carried by the other of said syringe and said first means, said shaft having an enlargement thereon which is sized and positioned to fit into the recess in said coupling attachment, whereby said syringe may be simply moved in and out of place in said block.

31. In a device as recited in claim 30, the further improvement wherein:

said block is made out of a resilient material and the width of the slot therein is less than the width of said syringe, whereby said syringe is held by the resiliency of said block.

32. In a device as recited in claim 30, the further improvement wherein:

(a) the slot in said block is open-topped, and (b) the recess in said coupling attachment is upwardly open, whereby said syringe may be simply lifted in and out of place in said block.

33. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement comprising:

(e) a first block on which said first means is carried, said first block having slots therein parallel to the direction of motion of said syringe; and (f) a plurality of bolts which pass through the slots in said first slotted block, whereby the amount by which the needle of said syringe protrudes through the aperture in said work plate when said syringe is in its second position can be adjusted.

34. In a device as recited in claim 33, the further improvement comprising third means for adjusting the position of said syringe in the horizontal plane and in the direction perpendicular to its direction of motion.

35. A device as recited in claim 34, wherein said third means comprises:

(a) a second block on which said first means is carried, said second block having slots therein perpendicular to the direction of motion of said syringe; and (b) a plurality of bolts which pass through the slots in said second block.

36. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement comprising:

(e) a first block on which said first means is carried, said first block having slots therein perpendicular to the direction of motion of said syringe; and (f) a plurality of bolts which pass through the slots in said first slotted block, whereby the position of said syringe is the horizontal plane and in the direction perpendicular to its direction of motion can be adjusted.

37. In a device as recited in claim 36, the further improvement comprising third means for adjusting the amount by which the needle of said syringe protrudes through the aperture in said work plate when said syringe is in its second position.

38. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement wherein:

(e) said syringe is journaled for rapid translational movement in an open-topped slot in a block mounted on said opposite side of said work plate;

(f) said block is made out of a resilient material; and (g) the width of the open-topped slot in said block is less than the width of said syringe, whereby said syringe is held against vertical motion by the resiliency of said block.

39. In an automatic injection device comprising:

(a) a work plate on which an animal to be injected can be positioned, said work plate having an aperture therein;

(b) a syringe mounted on the opposite side of said work plate from the side on which the animal to be injected is positioned during use of the device;

(c) first means for moving said syringe back and forth between a first position wherein said syringe is entirely withdrawn on said opposite side of said work plate and a second position wherein the needle of said syringe protrudes through the aperture in said work plate; and (d) second means for detecting the presence of an animal to be injected in position on said work plate and for activating said first means, the improvement comprising:

(e) third means for counting the number of times said first means has been actuated and (f) fourth means for shutting off the device when said first means has been actuated a preset number of times.

* * * * *